US012616829B2

(12) United States Patent
Ker et al.

(10) Patent No.: US 12,616,829 B2
(45) Date of Patent: May 5, 2026

(54) SYNCHRONIZED SAMPLE-AND-HOLD STIMULATION ARTIFACT REMOVAL FOR REAL-TIME CLOSED-LOOP ELECTRICAL STIMULATION AND RECORDING DEVICE

(71) Applicant: National Yang Ming Chiao Tung University, Hsinchu City (TW)

(72) Inventors: Ming-Dou Ker, Jhu-bei City (TW); Chung-Yu Wu, Hsinchu City (TW); Chi-Wei Huang, Hsinchu City (TW)

(73) Assignee: NATIONAL YANG MING CHIAO TUNG UNIVERSITY, Hsinchu City (TW)

( * ) Notice: Subject to any disclaimer, the term of this patent is extended or adjusted under 35 U.S.C. 154(b) by 272 days.

(21) Appl. No.: 18/545,016

(22) Filed: Dec. 19, 2023

(65) Prior Publication Data

US 2025/0195875 A1     Jun. 19, 2025

(51) Int. Cl.
   *A61N 1/00*       (2006.01)
   *A61N 1/02*       (2006.01)
   (Continued)

(52) U.S. Cl.
   CPC ........... *A61N 1/025* (2013.01); *A61N 1/0529* (2013.01); *A61N 1/36153* (2013.01)

(58) Field of Classification Search
   None
   See application file for complete search history.

(56) References Cited

U.S. PATENT DOCUMENTS 5,722,997  A  *  3/1998  Nedungadi ........ A61N 1/36521
                                          600/580
5,735,883  A  *  4/1998  Paul ..................... A61N 1/3712
                                          607/28
(Continued)

FOREIGN PATENT DOCUMENTS

TW          I667993  B      8/2019

OTHER PUBLICATIONS

Blum et al., "An Integrated System for Simultaneous, Multichannel Neuronal Stimulation and Recording," IEEE Trans. Circuits Syst. I: Regular Papers, vol. 54, No. 12, Dec. 2007, pp. 2608-2618.
(Continued)

*Primary Examiner* — William J Levicky
*Assistant Examiner* — Anant A Gupta
(74) *Attorney, Agent, or Firm* — Birch, Stewart, Kolasch & Birch, LLP

(57)          ABSTRACT

A real-time closed-loop electrical stimulation and recording device includes an electrical stimulator, a processor, two or more sample-and-hold protection circuits, and an analog front-end amplifier. The electrical stimulator is connected to a physiological tissue. The processor controls the protection circuits to sample and hold the first voltage of an analog physiological signal from a physiological tissue before the electrical stimulator generates a stimulation signal. The processor controls the protection circuits to block the analog physiological signal after the protection circuits hold the first voltage. The processor controls the protection circuits to sample and hold the second voltage of the analog physiological signal that replace the first voltage from the physiological tissue after the stimulation signal ends. The amplifier amplifies the first voltage or the second voltage to generate a detection signal and transmit the detection signal to the processor.

10 Claims, 4 Drawing Sheets

(51) Int. Cl.
    *A61N 1/05*      (2006.01)
    *A61N 1/36*      (2006.01)

(56)           References Cited

U.S. PATENT DOCUMENTS

| | | | |
|---|---|---|---|
| 6,473,648 B1 * | 10/2002 | Prutchi | A61N 1/36521 |
| | | | 607/28 |
| 2017/0273594 A1 | 9/2017 | Liu et al. | |
| 2020/0129766 A1 | 4/2020 | Sabes et al. | |
| 2020/0230418 A1 * | 7/2020 | Ahmadi | A61N 1/3606 |

OTHER PUBLICATIONS

Huang et al., "A CMOS Synchronized Sample-And-Hold Artifact Blanking Analog Front-End Local Field Potential Acquisition Unit With ±3.6-V Stimulation Artifact Tolerance and Monopolar Electrode-Tissue Impedance Measurement Circuit for Closed-Loop Deep Brain Stimulation SoCs", IEEE Trans. Circuits Syst. I: Regular Papers, Mar. 17, 2023, pp. 1-14 (total 17 pages).

Wu et al., "A 2.36μW/Ch CMOS 8-Channel EEG Acquisition Unit with Input Protection Circuits for Applications Under Transcranial Direct Current Stimulation", Proc. IEEE Biomed. Cir-cuits Syst. Conf. (BioCAS), 2019, total 4 pages.

* cited by examiner

SYNCHRONIZED SAMPLE-AND-HOLD STIMULATION ARTIFACT REMOVAL FOR REAL-TIME CLOSED-LOOP ELECTRICAL STIMULATION AND RECORDING DEVICE

BACKGROUND OF THE INVENTION

Field of the Invention

The invention relates to a synchronized sample-and-hold stimulation artifact removal recording and stimulation device, particularly to a real-time closed-loop electrical stimulation and recording device.

Description of the Related Art

A closed-loop biomedical electrical stimulation system includes an analog front-end physiological signal amplifier for measuring neural signals and a stimulator circuit for generating electrical stimulation. The closed-loop biomedical electrical stimulation system monitors the patient's neural signal characteristics as the basis for closed-loop control while applying high-voltage stimulation. With the evolution of integrated circuit processes, the required power supply voltage for the circuit gradually decreases. However, the withstand voltage of the components also decreases. High-voltage stimulation generates stimulation noise that contaminates the measured neural signals. High voltage larger than the withstand voltage of the component may cause irreversible damage to circuits, thereby affecting functionality or shortening the circuit's lifespan.

It is known that the analog front-end physiological signal amplifier adopts an input protection circuit to block stimulation noise. It disconnects the amplifier from the electrode during stimulation to prevent stimulation noise from entering the amplifier. However, it can only block positive voltage stimulation. During the blocking period, the brainwave signal in the moment of stimulation cannot be observed. Also, after the blocking period ends, a longer recovery time is needed for the physiological signal amplifier to return to its normal operation, resulting in significant waveform distortion.

In addition to the foregoing techniques, additional hardware circuits or software methods are used to obtain the waveform contaminated by stimulation noise from the output of the signal amplifier, obtain the stimulation noise from the contaminated waveform, and transmit the obtained stimulation noise to the input of the signal amplifier for counteraction based on negative feedback compensation. Therefore, additional hardware circuits and software methods are required to perform this function, causing a great amount of computational power consumption. The method can only separate stimulation noise with the same features. If the noise characteristics change, it is unable to eliminate the noise completely and prevent output saturation and component damage caused by excessive stimulation noise.

SUMMARY OF THE INVENTION

The invention provides a real-time closed-loop electrical stimulation and recording device, which avoids the output saturation or component damage of an amplifier caused by excessive voltage during high-voltage stimulation, reduces signal loss and nonlinear distortion caused by blocking a stimulation signal, and effectively blocks noise contamination caused by electrical stimulation without requiring a great amount of additional power consumption. The closed-loop electrical stimulation device can be easily applied and integrated into a system or a system-on-chip (SoC) using various processes rather than specialized high-voltage withstanding processes.

In an embodiment of the invention, a real-time closed-loop electrical stimulation and recording device is connected to a physiological tissue and provided. The closed-loop electrical stimulation device includes an electrical stimulator, a processor, two or more sample-and-hold protection circuits, and an analog front-end amplifier. The electrical stimulator is connected to the physiological tissue. The processor is connected to the electrical stimulator and configured to drive the electrical stimulator to generate a stimulation signal applied to the physiological tissue. The sample-and-hold protection circuits are connected to the physiological tissue and the processor. The processor controls the sample-and-hold protection circuits to sample and hold the first voltage of an analog physiological signal from the physiological tissue before the electrical stimulator generates the stimulation signal. The processor controls the sample-and-hold protection circuits to block the analog physiological signal after the sample-and-hold protection circuits hold the first voltage. The processor controls the sample-and-hold protection circuits to sample and hold the second voltage of the analog physiological signal that replace the first voltage from the physiological tissue after the stimulation signal ends. The analog front-end amplifier is connected to the sample-and-hold protection circuits and the processor and configured to receive and amplify the first voltage or the second voltage to generate a detection signal and transmit the detection signal to the processor.

In an embodiment of the invention, each of the sample-and-hold protection circuits is connected to a grounding terminal. The processor couples each of the sample-and-hold protection circuits to a grounding voltage of the grounding terminal after each of the sample-and-hold protection circuits samples and holds the first voltage. The physiological tissue is decoupled to the grounding voltage when the sample-and-hold protection circuits blocks the analog physiological signal. The processor decouples the sample-and-hold protection circuits to the grounding voltage when the sample-and-hold protection circuits sample and hold the second voltage.

In an embodiment of the invention, the sample-and-hold protection circuit includes a first electrical switch, a second electrical switch, at least one third electrical switch, and a capacitor. The first electrical switch and the capacitor are connected in series. The capacitor is connected between the analog front-end amplifier and the first electrical switch. The control terminal of the first electrical switch is connected to the processor. The first electrical switch is connected between the physiological tissue and the capacitor. The second electrical switch is connected between a node and the grounding terminal. The node is connected between the physiological tissue and the first electrical switch. The control terminal of the second electrical switch is connected to the processor. The third electrical switch is connected between the node and the physiological tissue. The control terminal of the third electrical switch is connected to the processor. When the processor turns on the first electrical switch and the third electrical switch and turns off the second electrical switch, the capacitor samples and holds the first voltage or the second voltage through the first electrical switch and the third electrical switch and the node is decoupled to the grounding voltage. When the processor turns off the first electrical switch and the third electrical switch and turns on the second electrical switch, the first electrical switch and the third electrical switch block the analog physiological signal, the node is coupled to the grounding voltage, and the physiological tissue is decoupled to the grounding voltage.

In an embodiment of the invention, the first electrical switch is an N-channel metal-oxide-semiconductor field-effect transistor (NMOSFET) and the second electrical switch is an N-channel metal-oxide-semiconductor field-effect transistor (NMOSFET) or a P-channel metal-oxide-semiconductor field-effect transistor (PMOSFET).

In an embodiment of the invention, the third electrical switch is an N-channel metal-oxide-semiconductor field-effect transistor (NMOSFET) for blocking a positive voltage or a P-channel metal-oxide-semiconductor field-effect transistor (NMOSFET) for blocking a negative voltage.

In an embodiment of the invention, the third electrical switch comprises an N-channel metal-oxide-semiconductor field-effect transistor (NMOSFET) and a P-channel metal-oxide-semiconductor field-effect transistor (NMOSFET) connected in series.

In an embodiment of the invention, the analog front-end amplifier includes a gain stage, a programmable bandwidth stage, and an analog-to-digital converter (ADC). The gain stage is connected to the sample-and-hold protection circuits and configured to receive and amplify the first voltage or the second voltage to generate a physiological amplified signal. The programmable bandwidth stage is coupled to the gain stage and configured to receive the physiological amplified signal and select and output the middle frequency component of the physiological amplified signal. The ADC is connected to the programmable bandwidth stage and the processor and configured to receive the middle frequency component of the physiological amplified signal, perform analog-to-digital conversion on the middle frequency component of the physiological amplified signal to generate the detection signal, and transmit the detection signal to the processor.

In an embodiment of the invention, the stimulation signal includes a negative pulse voltage or a positive pulse voltage.

In an embodiment of the invention, the stimulation signal includes a negative pulse voltage and a positive pulse voltage that are sequentially occur.

In an embodiment of the invention, the closed-loop electrical stimulation device further includes a conductor with isolators and electrodes. The conductor is arranged in the physiological tissue. The isolators and the electrodes are alternately arranged. The electrodes are respectively connected to the electrical stimulator and the sample-and-hold protection circuits and commonly connected to the physiological tissue.

To sum up, the real-time closed-loop electrical stimulation and recording device can block the stimulation signal of both positive and negative voltages, avoiding the output saturation or component damage of the amplifier caused by excessive voltage during high-voltage stimulation. The closed-loop electrical stimulation device synchronously samples and holds the physiological signal before the stimulation signal is generated, enabling the rapid recovery of the physiological signal after the stimulation signal ends. The closed-loop electrical stimulation device can reduce signal loss and nonlinear distortion caused by blocking the stimulation signal. By appropriately controlling the timing of the generation of the stimulation signal and the electrical switches of the protection circuit, it can effectively block noise contamination caused by electrical stimulation without requiring a great amount of additional power consumption. The closed-loop electrical stimulation device is highly energy-efficient, especially in applications of implantable biomedical systems. The closed-loop electrical stimulation device can be easily applied and integrated into a system or a system-on-chip (SoC) using various processes rather than specialized high-voltage withstanding processes.

Below, the embodiments are described in detail in cooperation with the drawings to make easily understood the technical contents, characteristics and accomplishments of the invention.

DETAILED DESCRIPTION OF THE INVENTION

Figure 1:
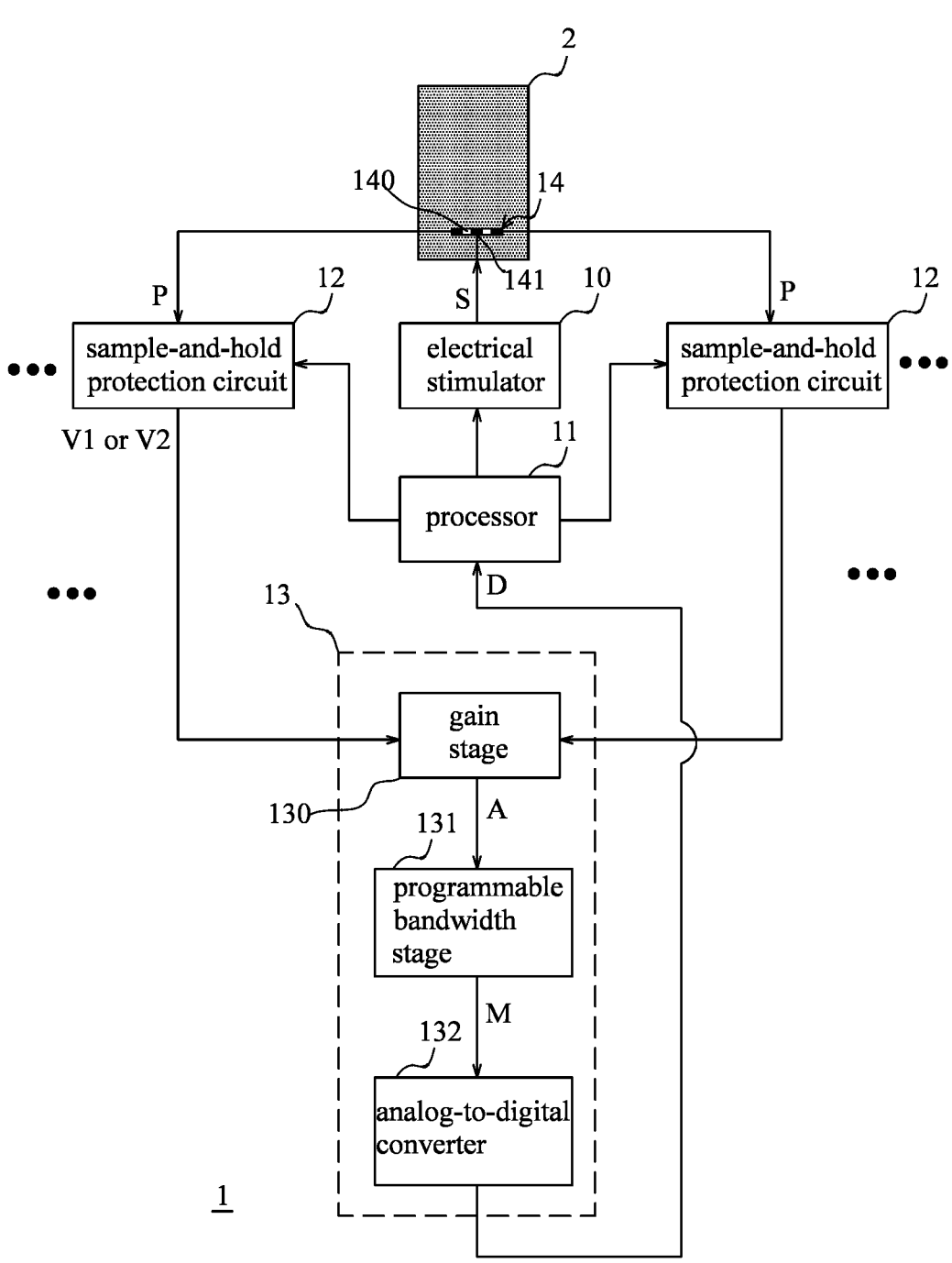
FIG. 1 is a diagram schematically illustrating a real-time closed-loop electrical stimulation and recording device according to an embodiment of the invention.

Reference will now be made in detail to embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, methods and apparatus in accordance with the present disclosure. It is to be understood that elements not specifically shown or described may take various forms well known to those skilled in the art. Many alternatives and modifications will be apparent to those skilled in the art, once informed by the present disclosure.

Unless otherwise specified, some conditional sentences or words, such as "can", "could", "might", or "may", usually attempt to express what the embodiment in the invention has, but it can also be interpreted as a feature, element, or step that may not be needed. In other embodiments, these features, elements, or steps may not be required.

Reference throughout this specification to "one embodiment" or "an embodiment" means that a particular feature, structure, or characteristic described in connection with the embodiment is included in at least one embodiment. Thus, the occurrences of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain terms are used throughout the description and the claims to refer to particular components. One skilled in the art appreciates that a component may be referred to using different names. This disclosure does not intend to distinguish between components that differ in name but not in function. In the description and in the claims, the term "comprise" is used in an open-ended fashion, and thus should be interpreted to mean "include, but not limited to." The phrases "be coupled to," "couples to," and "coupling to" are intended to encompass any indirect or direct connection.

Accordingly, if this disclosure mentions that a first device is coupled with a second device, it means that the first device may be directly or indirectly connected to the second device through electrical connections, wireless communications, optical communications, or other signal connections with/ without other intermediate devices or connection means.

The invention is particularly described with the following examples which are only for instance. Those skilled in the art will readily observe that numerous modifications and alterations of the device and method may be made while retaining the teachings of the invention. Accordingly, the following disclosure should be construed as limited only by the metes and bounds of the appended claims. In the whole patent application and the claims, except for clearly described content, the meaning of the articles "a" and "the" includes the meaning of "one or at least one" of the elements or components. Moreover, in the whole patent application and the claims, except that the plurality can be excluded obviously according to the context, the singular articles also contain the description for the plurality of elements or components. In the entire specification and claims, unless the contents clearly specify the meaning of some terms, the meaning of the article "wherein" includes the meaning of the articles "wherein" and "whereon". The meanings of every term used in the present claims and specification refer to a usual meaning known to one skilled in the art unless the meaning is additionally annotated. Some terms used to describe the invention will be discussed to guide practitioners about the invention. The examples in the present specification do not limit the claimed scope of the invention.

In the following description, a closed-loop electrical stimulation device will be described. The closed-loop electrical stimulation device can block the stimulation signal of both positive and negative voltages, avoiding the output saturation or component damage of an analog front-end amplifier caused by excessive voltage during high-voltage stimulation. The closed-loop electrical stimulation device synchronously samples and holds a physiological signal before a stimulation signal is generated, enabling the rapid recovery of the physiological signal after the stimulation signal ends. The closed-loop electrical stimulation device can reduce signal loss and nonlinear distortion caused by blocking the stimulation signal. By appropriately controlling the timing of the generation of the stimulation signal and the electrical switches of a sample-and-hold protection circuit, it can effectively block noise contamination caused by electrical stimulation without requiring a great amount of additional power consumption. The closed-loop electrical stimulation device is highly energy-efficient, especially in applications of implantable biomedical systems. The closed-loop electrical stimulation device can be easily applied and integrated into a system or a system-on-chip (SoC) using various processes rather than specialized high-voltage withstanding processes.

FIG. 1 is a diagram schematically illustrating a real-time closed-loop electrical stimulation and recording device according to an embodiment of the invention. Referring to FIG. 1, the real-time closed-loop electrical stimulation and recording device 1, connected to a physiological tissue 2, includes an electrical stimulator 10, a processor 11, two or more sample-and-hold protection circuits 12, and an analog front-end amplifier 13. For example, the physiological tissue 2 may be a brain tissue, but the invention is not limited thereto. The electrical stimulator 10 is connected to the physiological tissue 2. The processor 11 is connected to the electrical stimulator 10. The sample-and-hold protection circuits 12 are connected to the physiological tissue 2 and the processor 11. The analog front-end amplifier 13 is connected to the sample-and-hold protection circuits 12 and the processor 11. In some embodiments of the invention, the closed-loop electrical stimulation device 1 further includes a conductor 14 with isolators 140 and electrodes 141. The conductor 14 is arranged in the physiological tissue 2. The isolators 140 and the electrodes 141 are alternately arranged. The electrodes 141 are respectively connected to the electrical stimulator 10 and the sample-and-hold protection circuits 12 and commonly connected to the physiological tissue 2.

The processor 11 drives the electrical stimulator 10 to generate a stimulation signal S applied to the physiological tissue 2. The processor 11 controls the sample-and-hold protection circuits 12 to sample and hold the first voltage V1 of an analog physiological signal P from the physiological tissue 2 before the electrical stimulator 10 generates the stimulation signal S. Since the stimulation signal S is coupled to the analog physiological signal P via the isolators 140, the processor 11 controls the sample-and-hold protection circuits 12 to block the analog physiological signal P after the sample-and-hold protection circuits 12 hold the first voltage V1. The processor 11 controls the sample-and-hold protection circuits 12 to sample and hold the second voltage V2 of the analog physiological signal P that replace the first voltage V1 from the physiological tissue 2 after the stimulation signal S ends. The analog front-end amplifier 13 receives and amplifies the first voltage V1 or the second voltage V2 to generate a detection signal D and transmit the detection signal D to the processor 11.

In some embodiments of the invention, the analog front-end amplifier 13 includes a gain stage 130, a programmable bandwidth stage 131, and an analog-to-digital converter (ADC) 132. The gain stage 130 is connected to the sample-and-hold protection circuits 12. The programmable bandwidth stage 131 is coupled to the gain stage 130. The ADC 132 is connected to the programmable bandwidth stage 131 and the processor 11. The gain stage 130 receives and amplifies the first voltage V1 or the second voltage V2 to generate a physiological amplified signal A. The programmable bandwidth stage 131 receives the physiological amplified signal A and selects and outputs the middle frequency component M of the physiological amplified signal A. The ADC 132 receives the middle frequency component M of the physiological amplified signal A, performs analog-to-digital conversion on the middle frequency component M of the physiological amplified signal A to generate the detection signal D, and transmits the detection signal D to the processor 11.

Figure 2:
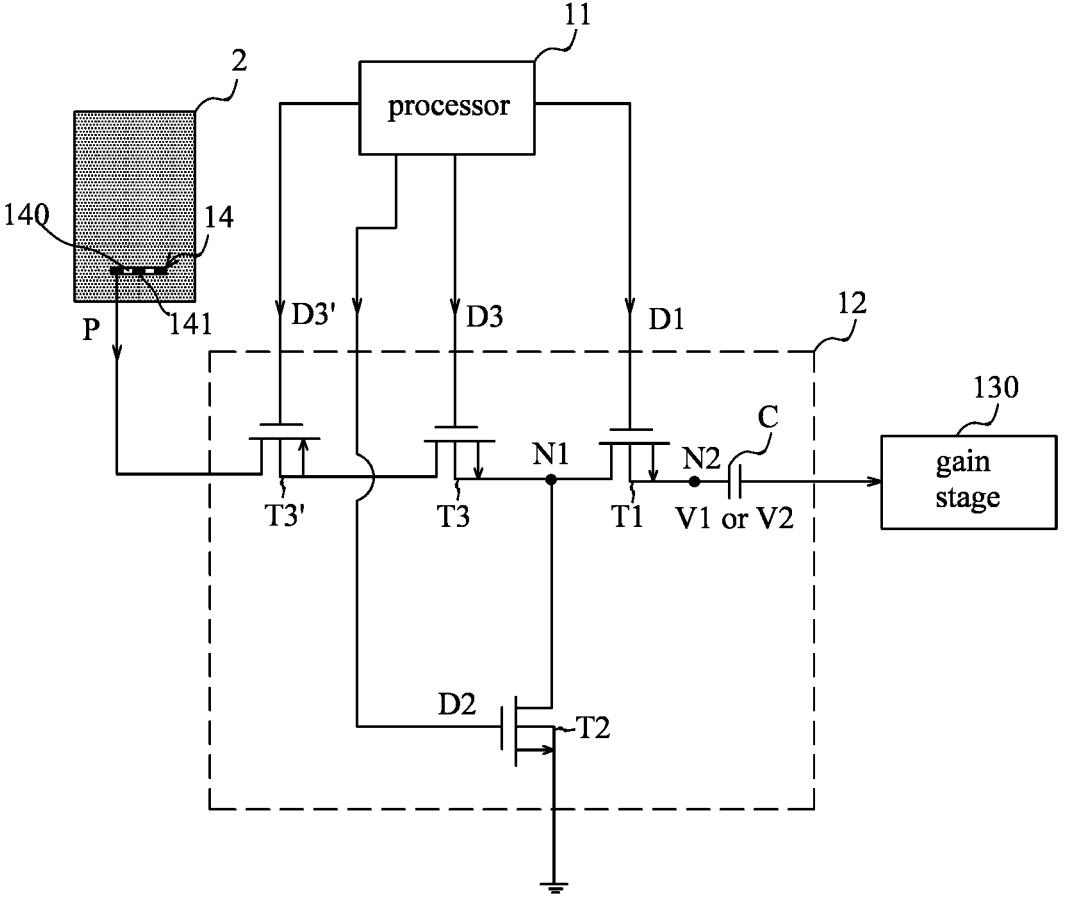
FIG. 2 is a diagram schematically illustrating a sample-and-hold protection circuit according to an embodiment of the invention.

FIG. 2 is a diagram schematically illustrating a sample-and-hold protection circuit according to an embodiment of the invention. Referring to FIG. 2, each of the sample-and-hold protection circuits 12 may be connected to a grounding terminal. The processor 11 couples each of the sample-and-hold protection circuits 12 to the grounding voltage of the grounding terminal after each of the sample-and-hold protection circuits 12 samples and holds the first voltage V1. The physiological tissue 2 is decoupled to the grounding voltage when the sample-and-hold protection circuits 12 blocks the analog physiological signal P. The processor 11 decouples the sample-and-hold protection circuits 12 to the grounding voltage when the sample-and-hold protection circuits 12 sample and hold the second voltage V2.

The sample-and-hold protection circuit 12 may include a first electrical switch T1, a second electrical switch T2, at least one third electrical switch, and a capacitor C. The first electrical switch T1 and the second electrical switch T2 may be, but not limited to, N-channel metal-oxide-semiconductor field-effect transistors (NMOSFETs). Alternatively, the second electrical switch T2 may be a P-channel metal-oxide-semiconductor field-effect transistor (PMOSFET) or a logic circuit. The embodiment exemplifies two third electrical switches T3 and T3' that include an N-channel metal-oxide-semiconductor field-effect transistor (NMOSFET) for blocking a positive voltage and a P-channel metal-oxide-semiconductor field-effect transistor (NMOSFET) for blocking a negative voltage connected in series. The first electrical switch T1 and the capacitor C are connected in series. The capacitor C is connected between the gain stage 130 of the analog front-end amplifier 13 and the first electrical switch T1. The control terminal of the first electrical switch T1 is connected to the processor 11. The first electrical switch T1 is connected between the physiological tissue 2 and the capacitor C. The second electrical switch T2 is connected between a node N1 and the grounding terminal. The node N1 is connected between the physiological tissue 2 and the first electrical switch T1. The control terminal of the second electrical switch T2 is connected to the processor 11. The third electrical switches T3 and T3' are connected between the node N1 and the physiological tissue 2. The control terminals of the third electrical switches T3 and T3' are connected to the processor 11.

When the processor 11 turns on the first electrical switch T1 and the third electrical switches T3 and T3' and turns off the second electrical switch T2, the capacitor C samples and holds the first voltage V1 or the second voltage V2 through the first electrical switch T1 and the third electrical switches T3 and T3' and the node N1 is decoupled to the grounding voltage. When the processor 11 turns off the first electrical switch T1 and the third electrical switches T3 and T3' and turns on the second electrical switch T2, the first electrical switch T1 and the third electrical switches T3 and T3' block the analog physiological signal P, the node N1 is coupled to the grounding voltage, and the physiological tissue 2 is decoupled to the grounding voltage. In other words, the first electrical switch T1 dominates the timing of sampling and holding the first voltage V1 of the physiological signal P. The second electrical switch T2 couples or decouples the node N1 to the grounding voltage. The third electrical switches T3 and T3' pass or block the physiological signal P. In such a case, the stimulation signal S includes a negative pulse voltage and a positive pulse voltage that are sequentially occur. In other embodiments, the stimulation signal S includes a negative pulse voltage or a positive pulse voltage. When the stimulation signal S merely includes a negative pulse voltage, the sample-and-hold protection circuit 12 includes one third electrical switch T3' implemented with a PMOSFET. When the stimulation signal S merely includes a positive pulse voltage, the sample-and-hold protection circuit 12 includes one third electrical switch T3 implemented with an NMOSFET. As a result, the closed-loop electrical stimulation device can block the stimulation signal of both positive and negative voltages, avoiding the output saturation or component damage of the amplifier caused by excessive voltage during high-voltage stimulation. The closed-loop electrical stimulation device can be easily applied and integrated into a system or a SoC using various processes rather than specialized high-voltage withstanding processes. By appropriately controlling the timing of the generation of the stimulation signal and the electrical switches of the protection circuit, it can effectively block noise contamination caused by electrical stimulation without requiring a great amount of additional power consumption.

Figure 3:
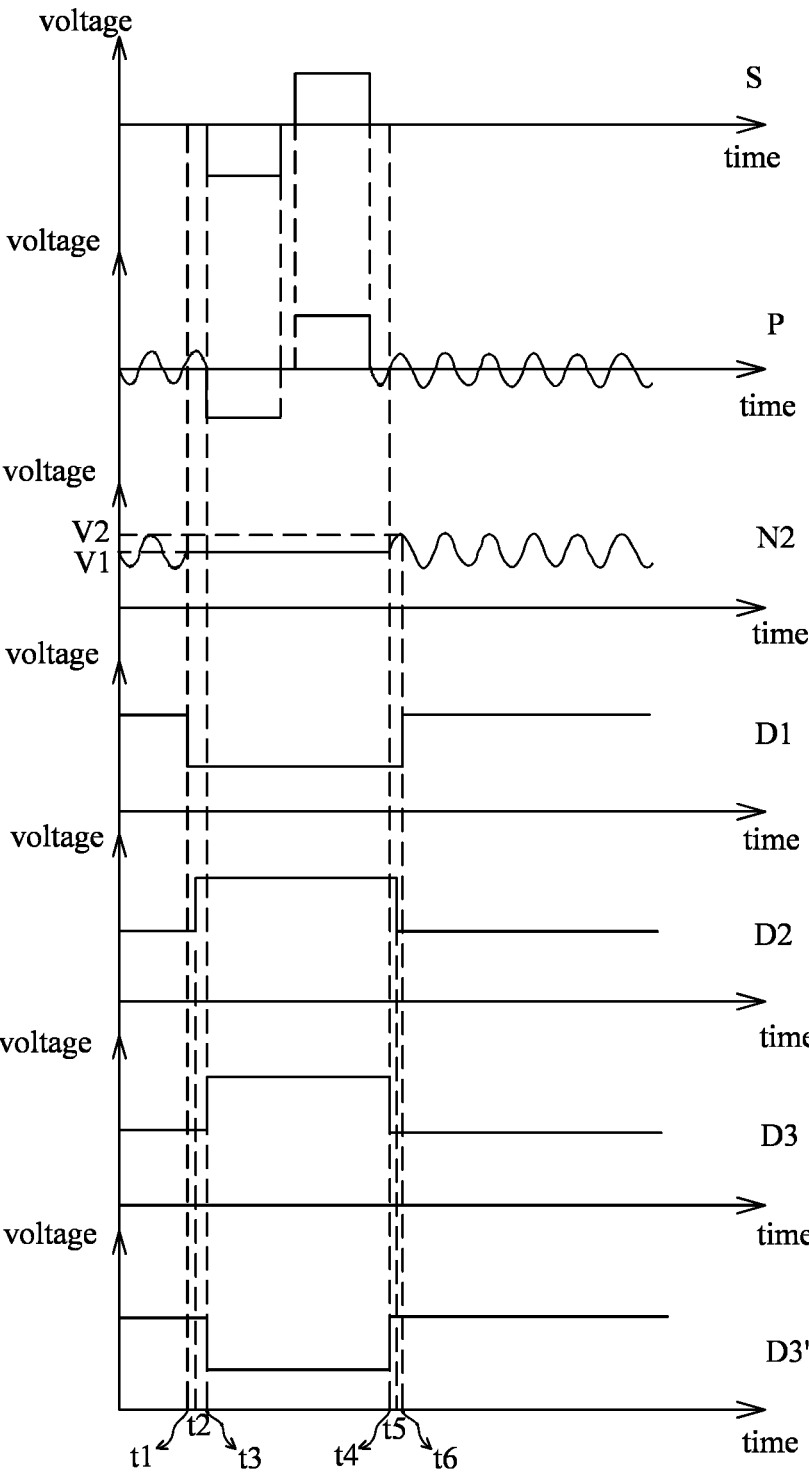
FIG. 3 is a diagram schematically illustrating the waveforms of nodes in FIG. 1 and FIG. 2 according to an embodiment of the invention.

FIG. 3 is a diagram schematically illustrating the waveforms of nodes in FIG. 1 and FIG. 2 according to an embodiment of the invention. Please refer to FIG. 1, FIG. 2, and FIG. 3. FIG. 3 shows the waveforms of the stimulation signal S, the physiological signal P, a node N2 between the capacitor C and the first electrical switch T1, a first digital signal D1, a second digital signal D2, and third digital signals D3 and D3' at time points t1, t2, t3, t4, t5, and t6 that sequentially occur. The first digital signal D1 generated by the processor 11 is transmitted to the control terminal of the first electrical switch T1 and configured to switch the first electrical switch T1. The second digital signal D2 generated by the processor 11 is transmitted to the control terminal of the second electrical switch T2 and configured to switch the second electrical switch T2. The third digital signals D3 and D3' generated by the processor 11 are respectively transmitted to the control terminals of the third electrical switch T3 and T3' and configured to switch the third electrical switches T3 and T3'.

Before the stimulation signal S is generated, time point t1 occurs. At time point t1, the processor 11 turns on the first electrical switch T1 and the third electrical switches T3 and T3' and turns off the second electrical switch T2, the capacitor C samples the first voltage V1 through the first electrical switch T1 and the third electrical switches T3 and T3', and the node N1 is decoupled to the grounding voltage. Simultaneously, the processor 11 switches the first electrical switch T1 from an on state to an off state and the capacitor C holds the first voltage V1. At time point t2, the processor 11 switches the second electrical switch T2 from an off state to an on state such that the node N1 is coupled to the grounding voltage for elimination of transient coupling. At time point t3, the stimulation signal S is generated, the processor 11 switches the third electrical switches T3 and T3' from an on state to an off state to block the physiological signal P, and the physiological tissue 2 is decoupled to the grounding voltage. The third electrical switch T3 is used to block the positive pulse voltage of the physiological signal P. The third electrical switch T3' is used to block the negative pulse voltage of the physiological signal P.

After the stimulation signal S ends, time point t4 occurs. At time point t4, the processor 11 switches the third electrical switches T3 and T3' from an off state to an on state to pass the physiological signal P such that the physiological signal P is coupled to the node N1. At time point t5, the processor 11 switches the second electrical switch T2 from an on state to an off state such that the node N1 is decoupled to the grounding voltage. At time point t6, the processor 11 switches the first electrical switch T1 from an off state to an on state such that the capacitor C samples and holds the second voltage V2 that replaces the first voltage V1 through the first electrical switch T1 and the third electrical switches T3. Since the first voltage V1 is closer to the second voltage V2 than the grounding voltage, the physiological signal P can be rapidly recovered to reduce signal loss and nonlinear distortion caused by blocking the stimulation signal S.

Figure 4:
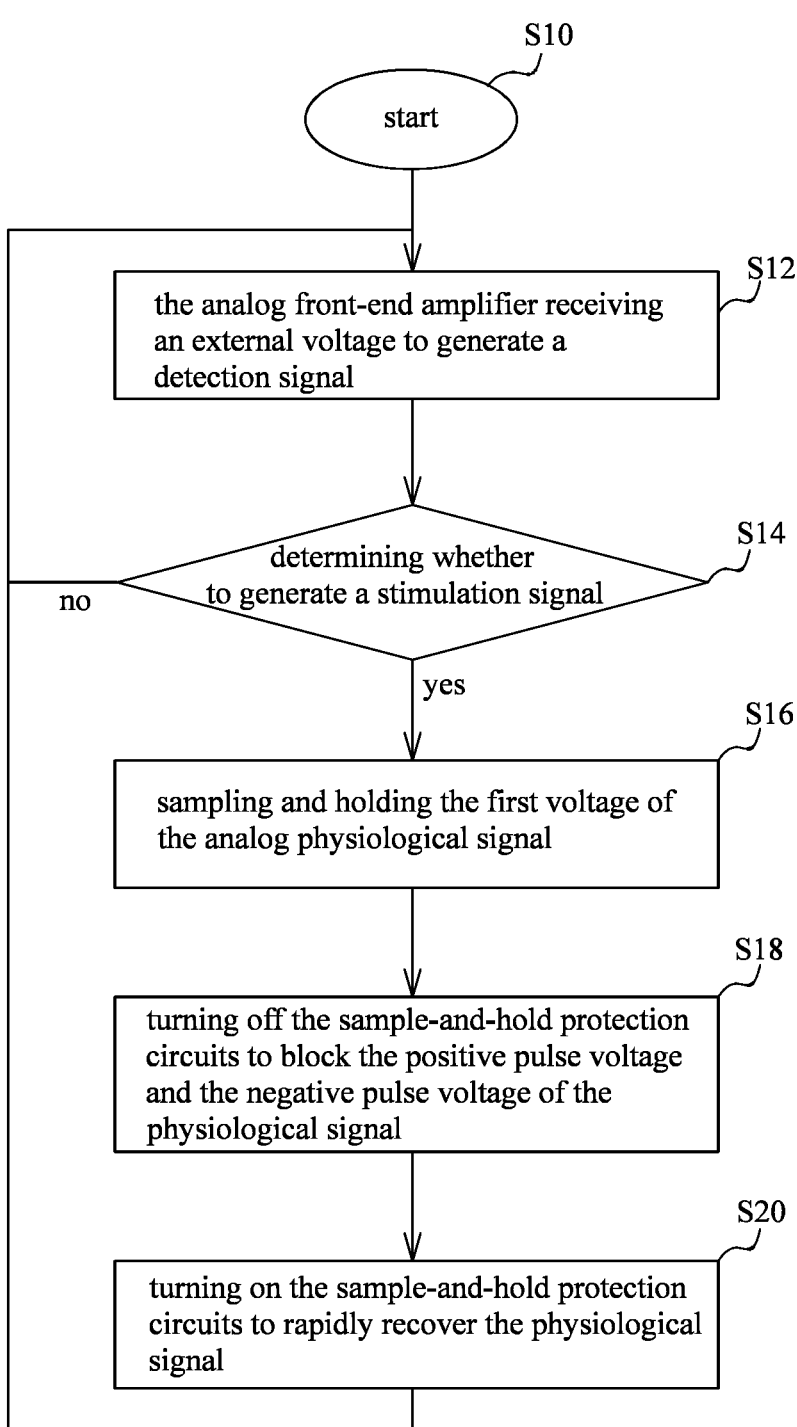
FIG. 4 is a flowchart of operating a real-time closed-loop electrical stimulation and recording device according to an embodiment of the invention.

FIG. 4 is a flowchart of operating a real-time closed-loop electrical stimulation and recording device according to an embodiment of the invention. Refer to FIG. 1, FIG. 3, and FIG. 4. In Step S10, the real-time closed-loop electrical stimulation and recording device 1 starts. In Step S12, the analog front-end amplifier 13 receives an external voltage to generate a detection signal D. In Step S14, the processor 11 receives the detection signal D to determine whether to drive the electrical stimulator to generate a stimulation signal S. If the result is no, the process proceeds to Step S 12. If the result is yes, the process proceeds to Step S16. In Step S16, the sample-and-hold protection circuits 12 sample and hold the first voltage V1 of the analog physiological signal P at time points t1 and t2. In Step S18, the sample-and-hold protection circuits 12 are turned off to block the positive pulse voltage and the negative pulse voltage of the physiological signal P at time point t3. In Step S20, the sample-and-hold protection circuits 12 are turned on to rapidly recover the physiological signal P at time points t4, t5, and t6. After Step S20, the process returns to Step S12.

According to the embodiments provided above, the closed-loop electrical stimulation device can block the stimulation signal of both positive and negative voltages, avoiding the output saturation or component damage of the amplifier caused by excessive voltage during high-voltage stimulation. The closed-loop electrical stimulation device synchronously samples and holds the physiological signal before the stimulation signal is generated, enabling the rapid recovery of the physiological signal after the stimulation signal ends. The closed-loop electrical stimulation device can reduce signal loss and nonlinear distortion caused by blocking the stimulation signal. By appropriately controlling the timing of the generation of the stimulation signal and the electrical switches of the protection circuit, it can effectively block noise contamination caused by electrical stimulation without requiring a great amount of additional power consumption. The closed-loop electrical stimulation device is highly energy-efficient, especially in applications of implantable biomedical systems.

The embodiments described above are only to exemplify the invention and not to limit the scope of the invention. Therefore, any equivalent modification or variation according to the shapes, structures, features, or spirit disclosed by the invention is to be also included within the scope of the invention.

What is claimed is:

1. A real-time closed-loop electrical stimulation and recording device, configured to be connected to a physiological tissue, comprising:

an electrical stimulator configured to be connected to the physiological tissue;

a processor connected to the electrical stimulator and configured to drive the electrical stimulator to generate a stimulation signal applied to the physiological tissue;

two or more sample-and-hold protection circuits configured to be connected to the physiological tissue and the processor, wherein the processor controls the sample-and-hold protection circuits to sample and hold a first voltage of an analog physiological signal from the physiological tissue before the electrical stimulator generates the stimulation signal, the processor controls the sample-and-hold protection circuits to block the analog physiological signal after the sample-and-hold protection circuits hold the first voltage, and the processor controls the sample-and-hold protection circuits to sample and hold a second voltage of the analog physiological signal that replaces the first voltage from the physiological tissue after the stimulation signal ends; and an analog front-end amplifier connected to the sample-and-hold protection circuits and the processor and configured to receive and amplify the first voltage or the second voltage to generate a detection signal and transmit the detection signal to the processor.

2. The real-time closed-loop electrical stimulation and recording device according to claim 1, wherein each of the sample-and-hold protection circuits is connected to a grounding terminal, the processor couples each of the sample-and-hold protection circuits to a grounding voltage of the grounding terminal after each of the sample-and-hold protection circuits samples and holds the first voltage, the physiological tissue is decoupled to the grounding voltage when the sample-and-hold protection circuits blocks the analog physiological signal, and the processor decouples the sample-and-hold protection circuits to the grounding voltage when the sample-and-hold protection circuits sample and hold the second voltage.

3. The real-time closed-loop electrical stimulation and recording device according to claim 2, wherein the sample-and-hold protection circuit comprises:

a first electrical switch and a capacitor connected in series, wherein the capacitor is connected between the analog front-end amplifier and the first electrical switch, a control terminal of the first electrical switch is connected to the processor, and the first electrical switch is configured to be connected between the physiological tissue and the capacitor;

a second electrical switch connected between a node and the grounding terminal, the node is configured to be connected between the physiological tissue and the first electrical switch, and a control terminal of the second electrical switch is connected to the processor; and at least one third electrical switch configured to be connected between the node and the physiological tissue, and a control terminal of the at least one third electrical switch is connected to the processor;

wherein when the processor turns on the first electrical switch and the at least one third electrical switch and turns off the second electrical switch, the capacitor samples and holds the first voltage or the second voltage through the first electrical switch and the at least one third electrical switch and the node is decoupled to the grounding voltage;

wherein when the processor turns off the first electrical switch and the at least one third electrical switch and turns on the second electrical switch, the first electrical switch and the at least one third electrical switch block the analog physiological signal, the node is coupled to the grounding voltage, and the physiological tissue is decoupled to the grounding voltage.

4. The real-time closed-loop electrical stimulation and recording device according to claim 3, wherein the first electrical switch is an N-channel metal-oxide-semiconductor field-effect transistor (NMOSFET) and the second electrical switch is an N-channel metal-oxide-semiconductor field-effect transistor (NMOSFET) or a P-channel metal-oxide-semiconductor field-effect transistor (PMOSFET).

5. The real-time closed-loop electrical stimulation and recording device according to claim 3, wherein, the at least one third electrical switch is an N-channel metal-oxide-semiconductor field-effect transistor (NMOSFET) for blocking a positive voltage or a P-channel metal-oxide-semiconductor field-effect transistor (NMOSFET) for blocking a negative voltage.

6. The real-time closed-loop electrical stimulation and recording device according to claim 3, wherein the at least one third electrical switch comprises an N-channel metal-oxide-semiconductor field-effect transistor (NMOSFET) and a P-channel metal-oxide-semiconductor field-effect transistor (NMOSFET) connected in series.

7. The real-time closed-loop electrical stimulation and recording device according to claim 1, wherein the analog front-end amplifier comprises:

a gain stage connected to the sample-and-hold protection circuits and configured to receive and amplify the first voltage or the second voltage to generate a physiological amplified signal;

a programmable bandwidth stage coupled to the gain stage and configured to receive the physiological amplified signal and select and output a middle frequency component of the physiological amplified signal; and an analog-to-digital converter (ADC) connected to the programmable bandwidth stage and the processor and configured to receive the middle frequency component of the physiological amplified signal, perform analog-to-digital conversion on the middle frequency component of the physiological amplified signal to generate the detection signal, and transmit the detection signal to the processor.

8. The real-time closed-loop electrical stimulation and recording device according to claim 1, wherein the stimulation signal comprises a negative pulse voltage or a positive pulse voltage.

9. The real-time closed-loop electrical stimulation and recording device according to claim 1, wherein the stimulation signal comprises a negative pulse voltage and a positive pulse voltage that sequentially occur.

10. The real-time closed-loop electrical stimulation and recording device according to claim 1, further comprises a conductor with isolators and electrodes, wherein the conductor is configured to be arranged in the physiological tissue, the isolators and the electrodes are alternately arranged, the electrodes are respectively connected to the electrical stimulator and the sample-and-hold protection circuits and commonly configured to be connected to the physiological tissue.

\* \* \* \* \*